United States Patent
Hsieh et al.

(10) Patent No.: US 11,771,847 B2
(45) Date of Patent: Oct. 3, 2023

(54) ASSEMBLY METHOD OF APPARATUS FOR PRESSURIZED LIQUID TRANSFUSION

(71) Applicant: MICROBASE TECHNOLOGY CORP., Taoyuan (TW)

(72) Inventors: Shu-Pin Hsieh, Taoyuan (TW); Yi-Tong Chen, Taoyuan (TW); Yi-Ting Lin, Taoyuan (TW); Po-Chuan Chen, Taoyuan (TW); Chiu-Ju Shen, Taoyuan (TW)

( * ) Notice: Subject to any disclaimer, the term of this patent is extended or adjusted under 35 U.S.C. 154(b) by 722 days.

(21) Appl. No.: 16/343,403

(22) PCT Filed: Nov. 6, 2017

(86) PCT No.: PCT/CN2017/109593
§ 371 (c)(1),
(2) Date: Apr. 18, 2019

(87) PCT Pub. No.: WO2018/082702
PCT Pub. Date: May 11, 2018

(65) Prior Publication Data
US 2019/0328981 A1    Oct. 31, 2019

Related U.S. Application Data

(60) Provisional application No. 62/418,174, filed on Nov. 6, 2016, provisional application No. 62/418,195, filed on Nov. 6, 2016.

(51) Int. Cl.
*A61M 11/00* (2006.01)
*B05B 1/02* (2006.01)
(Continued)

(52) U.S. Cl.
CPC ......... *A61M 11/007* (2014.02); *A61M 11/003* (2014.02); *A61M 15/009* (2013.01);
(Continued)

(58) Field of Classification Search
CPC .............. A61M 11/007; A61M 15/009; A61M 2205/0216; A61M 2205/121;
(Continued)

(56) References Cited

U.S. PATENT DOCUMENTS

| 4,150,794 A | 4/1979 | Higgins |
| 2003/0148030 A1* | 8/2003 | Vernon, Jr. ............ B65D 39/04 427/255.28 |

(Continued)

FOREIGN PATENT DOCUMENTS

| CN | 1921949 A | 2/2007 |
| CN | 202052680 U | 11/2011 |

(Continued)

OTHER PUBLICATIONS

Boehringer Ingelheim, CN 1921949A translation, 2004 (Year: 2004).*

(Continued)

*Primary Examiner* — Timothy A Stanis
(74) *Attorney, Agent, or Firm* — OPES IP Consulting Co. Ltd.

(57) ABSTRACT

An assembly method of an apparatus suitable for pressurized liquid transfusion is disclosed. In one step, a nozzle is to be inserted into the through hole of an elastomeric ring. Because the dimension of the nozzle is larger than the through hole, the internal wall of the elastomeric ring is tensioned and deformed so as to fit the nozzle. In one step, the elastomeric ring along with the nozzle is inserted into a receptacle. The dimension of the outer contour of the elastomeric ring needs to be decreased so as to be accommodated by the receptacle. Due to the flexibility of the elastomeric ring, it resumes at least partially to its original shape. Therefore, proper seal is created and maintained between the elastomeric ring and the nozzle such that leakage and pressure loss may be prevented. The foregoing (Continued)

is capable of working under high-pressured environment for prolonged use.

18 Claims, 15 Drawing Sheets

(51) Int. Cl.
    *A61M 15/00*     (2006.01)
    *A61M 31/00*     (2006.01)
    *B05B 1/26*     (2006.01)
    *B05B 1/10*     (2006.01)
    *B05B 11/10*     (2023.01)
    *B05B 1/34*     (2006.01)
    *B05B 11/00*     (2023.01)

(52) U.S. Cl.
    CPC ........ *A61M 15/0065* (2013.01); *A61M 31/00* (2013.01); *B05B 1/02* (2013.01); *B05B 1/10* (2013.01); *B05B 1/26* (2013.01); *B05B 1/34* (2013.01); *B05B 11/109* (2023.01); *B05B 11/1074* (2023.01); *A61M 2205/0216* (2013.01); *A61M 2205/0222* (2013.01); *A61M 2205/0238* (2013.01); *A61M 2205/121* (2013.01); *A61M 2207/00* (2013.01); *A61M 2210/0625* (2013.01); *B05B 11/0038* (2018.08)

(58) Field of Classification Search
    CPC ........ A61M 2207/00; B05B 1/10; B05B 1/26; B05B 1/02; B05B 1/34; B05B 11/0038
    See application file for complete search history.

(56) References Cited

U.S. PATENT DOCUMENTS

| | | | |
|---|---|---|---|
| 2004/0164186 A1 | 8/2004 | Kladders et al. | |
| 2006/0054165 A1 | 3/2006 | Hughes et al. | |
| 2006/0213514 A1* | 9/2006 | Price | A61M 15/0028 128/203.15 |
| 2007/0252022 A1* | 11/2007 | Benstead | E03C 1/084 239/590.5 |
| 2010/0022962 A1* | 1/2010 | Bierman | A61M 25/02 604/180 |

FOREIGN PATENT DOCUMENTS

| | | |
|---|---|---|
| CN | 203002553 U | 6/2013 |
| CN | 103769324 A | 5/2014 |
| CN | 205386506 U | 7/2016 |
| EP | 2044967 A1 | 4/2009 |
| WO | WO2007051536 A1 | 5/2007 |

OTHER PUBLICATIONS

Office action by CNIPA, dated Feb. 3, 2020.
Extended European search report from EPO, dated Jul. 6, 2020.
Office action from CNIPA, dated Sep. 27, 2020.
The internationl search report and the written opinion of the International Search Authority, dated Feb. 6, 2018, whole document, SIPO as ISA.
Office Action communication from TIPO, dated Jan. 17, 2019.
Office Action communication from TIPO, dated Sep. 11, 2018.

* cited by examiner

US 11,771,847 B2

ASSEMBLY METHOD OF APPARATUS FOR PRESSURIZED LIQUID TRANSFUSION

CROSS REFERENCE TO RELATED APPLICATION

The present application claims priority to PCT Application PCT/CN2017/109593 filed on Nov. 6, 2017, which claims priority to U.S. Provisional Application Ser. No. 62/418,174 filed on Nov. 6, 2016 and U.S. Provisional Application Ser. No. 62/418,195 filed on Nov. 6, 2016, which are hereby incorporated by reference in their entirety.

FIELD

The present disclosure relates to an assembly method of a nebulizer component and more particularly to an assembly method of an apparatus suitable for pressurized liquid transfusion.

BACKGROUND OF THE INVENTION

Aerosolizer, also known as nebulizer or atomizer, is used to deliver medication to patients for inhalation. Particularly, liquid medicament is broken down into aerosol of fine particles/droplets for easier and more efficient inhalation and absorption. The particle size may be adjusted depending on different respiratory conditions such as Chronic Obstructive Pulmonary Disease (COPD) or asthma, or depending on the requirement of the liquid medicament itself. Also, it is important that a patient receives the same amount of medication in each treatment. In other words, an aerosolizer should be able to deliver exact dosage(s) of medication having a fixed average particle size in every respective operation. Accordingly, a therapeutically effective amount of the medicament can be administrated to the patient accurately to reduce waste and risks of overdosing.

Referring to FIG. 1, an exemplary aerosolizer includes an upper casing, a lower casing, a nozzle assembly, a tube, a biasing element and a storage container. During preparation, the biasing element, such as a spring, is tensioned by the relative movement of the upper casing and the lower casing. Meanwhile, a fixed amount of liquid medicament is drawn from the storage container by the tube, ready to be aerosolized. When the aerosolizer is actuated, a force generated by the un-tensioned biasing element pushes the fixed amount of liquid medicament towards and through the nozzle assembly. As such, the resulting aerosol exits the aerosolizer for inhalation. Another exemplary aerosolizer and the operation mechanism thereof can be referenced to the disclosure in U.S. Pat. No. 5,964,416 (U.S. patent application Ser. No. 08/726,219).

As shown in FIG. 1, pressurized liquid medicament travels in the direction from A to A' and from a high pressure end to a low pressure end. As such, liquid medicament is drawn and forced into the nozzle assembly, through which aerosol is generated and expelled out. During aerosolization, it is crucial that proper seal is maintained between all the components. Otherwise, aerosolization effect may be compromised. For example, a leak at the nozzle assembly may lead to pressure loss, which can result in delivery of unprecise dosage or inappropriate aerosol particle size. In order to avoid such issues, components of the aerosolizer must be manufactured and assembled with heightened caution and precision. However, due to the miniature size of the aerosolizer components, usually in the scale of millimeters or less, achieving proper seal tends to be difficult and costly. Moreover, components of different geometric shapes and miniature sizes may be more prone to wear and tear in a high-pressure (usually between 5 and 50 MPa, which is about 50 to 500 bar) environment.

The present disclosure aims to provide a simplified design of the aerosolizer structure, including certain components therein, aerosolizer in order to achieve precise and effective dosage control aerosolize with less effort. The life of the aerosolizer may also be extended due to the novel design of the present invention. Accordingly, less effort and resource are needed for the manufacturing and assembling of the aerosolizers.

SUMMARY OF THE INVENTION

The present disclosure concerns an apparatus suitable for pressurized liquid transfusion. Proper seal between certain components of the apparatus is required in order to prevent liquid leak and pressure loss. Accordingly, the apparatus includes an elastomeric ring and a nozzle received therein. The combination thereof is then received by a receptacle covered by a cap. A casing and a check nut are further provided to enclose and secure the foregoing elements within. Pressurized liquid medicament is directed to pass through the apparatus for aerosolization. More particularly, aerosolization takes place at the nozzle. Based on the configuration of the present disclosure, a fixed amount of liquid medicament enters the nozzle in each actuation. A correspondingly same amount of aerosol leaves the nozzle where there is no or negligible residue or loss of the liquid medicament inside the apparatus system, e.g., between the components. The resulting aerosolizer provides precise dosage(s) of medication in each actuation. Also, the life of the aerosolizer may be prolonged because the components thereof are less prone to corrosion due to liquid permeated therebetween.

At least watertight seal is required inside the aerosolizer. Preferably, vacuum or airtight seal is preferred between the elastomeric ring and the nozzle, and between the elastomeric ring and the cap. In certain embodiments, portions of the surface of the elastomeric ring or the nozzle that are in contact with each other need to have certain physical or chemical characteristic. For example, such surfaces may be processed to become uniformly smooth, in a micrometer scale, to increase the contacting area therebetween. The foregoing results in less gap therebetween, which improves seal between the elastomeric ring and the nozzle and/or cap. In other examples, a bond may be created at such surfaces by chemical treatment. In yet some other examples, an interface layer may be applied so as to increase adherence between the elastomeric ring and the nozzle and/or cap. Such layer may enhance the adherence or minimize the gap therebetween. In addition, in certain embodiments such layer may be removed without damaging the elastomeric ring, the nozzle or the cap.

A method for assembling the apparatus suitable for pressurized liquid transfusion is also disclosed. The components of the apparatus is specifically designed and dimensioned such that proper seal may be achieved. For example, the width of the nozzle is larger than the width of the through hole of the elastomeric ring. Moreover, the diameter of the elastomeric ring is larger than the internal diameter of the receptacle at corresponding positions. As such, the elastomeric ring needs to be tensioned/over-tensioned to accommodate or to be accommodated by other components. The compressible nature of the elastomeric ring further improves seal with the nearby components. Additional steps may also be taken to expel air between the elastomeric ring and the nozzle to create a vacuum. Further, processing or treatment may be applied to the elastomeric ring or the nozzle to change the physical or chemical characteristic of their surfaces. An exemplary processing/treatment is wetting, which may be the application of an agent to the elastomeric ring such that intermolecular interaction is created/enhanced between the elastomeric ring and the nozzle/cap. Alternatively, the elastomeric ring or the nozzle may be manufactured with specific processed characteristics so no subsequent processing/treatment is needed.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed. Certain parts of the drawings are exaggerated for explanation purposes and shall not be considered limiting unless otherwise specified.

Figure 1:
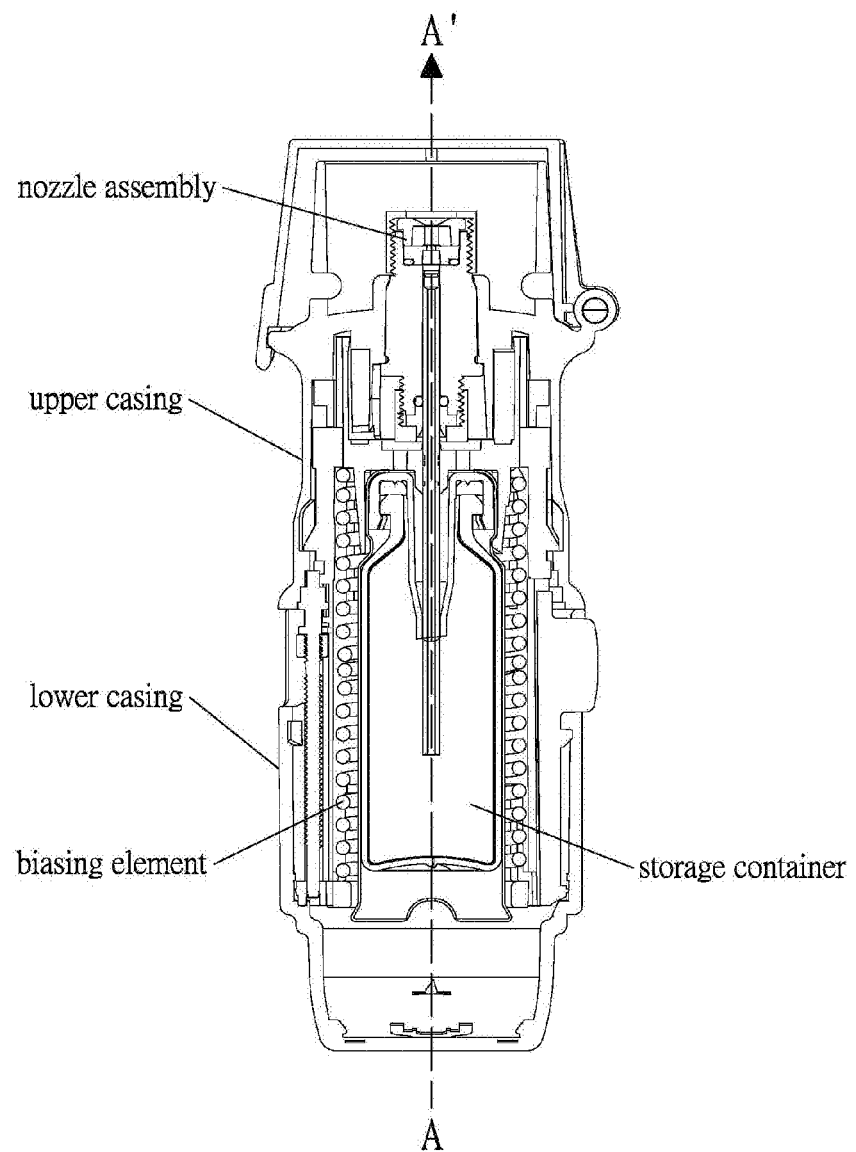
FIG. 1 is a cross section view of an exemplary aerosolizer according to the present disclosure.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention. Any reference signs in the claims shall not be construed as limiting the scope. Like reference symbols in the various drawings indicate like elements.

DETAILED DESCRIPTION OF THE PREFERRED EMBODIMENTS

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus in accordance with the present disclosure. It is to be understood that elements not specifically shown or described may take various forms. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise. Furthermore, relative terms, such as "bottom" and "top," may be used herein to describe one element's relationship to other elements as illustrated in the Figures.

It will be understood that elements described as "under" or "below" other elements would then be oriented "over" or "above" the other elements. The exemplary terms "under" or "below" can, therefore, encompass both an orientation of over and under.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
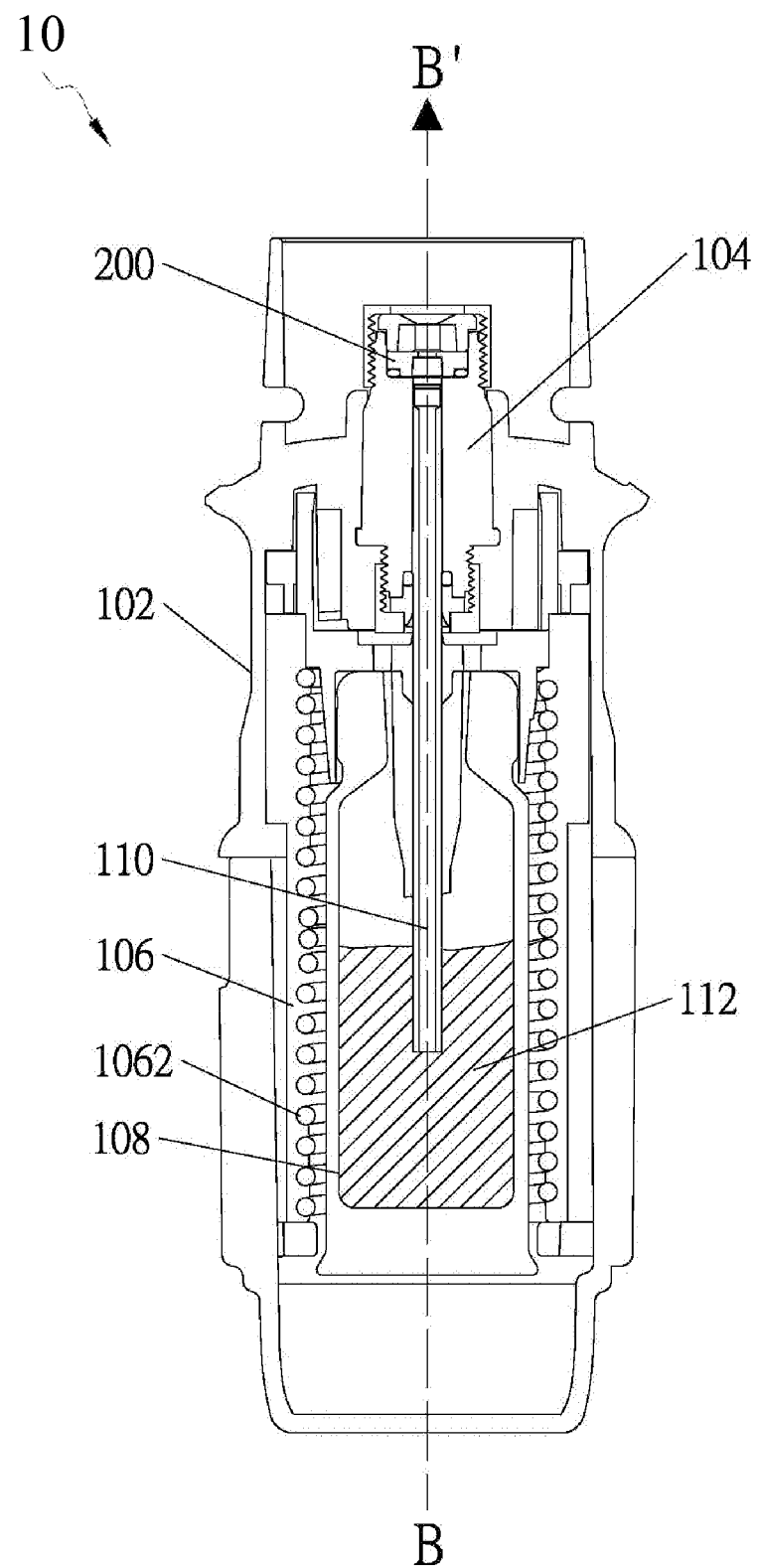
FIG. 2 is a cross section view of another exemplary aerosolizer according to the present disclosure.

FIG. 2 is a cross-sectional view of another exemplary aerosolizer according to the present disclosure. Here, the aerosolizer 10 includes a housing 102 with a pump chamber 104 and a spring chamber 106. A biasing element 1062, such as a spring, is coupled to the housing 102, and more particularly is mounted in the spring chamber 106. The spring chamber 106 also holds a storage container 108 where liquid medicament 112 is stored. Such liquid medicament 112 can be drawn from the storage container 108 via a tube 110 in response to a pre-actuation of the aerosolizer 10. Particularly, prior to actuation, the housing 102 is rotated. The spring 1062 is adapted to respond to such rotation by tensioning. Correspondingly, the liquid medicament 112 is drawn from the storage container 108 into the pump chamber 104 ready to be aerosolized. The aerosolization process starts when the aerosolizer 10 is actuated. When actuated, a release mechanism (not shown) is triggered and the spring 1062 is released from the tensioned state to the untensioned state. The foregoing operation results in a force pushing the liquid medicament 112 through a transfusion apparatus 200 at the pump chamber 104. Consequently, aerosolized liquid medicament, such as aqueous solution or ethanoic solution, exits the transfusion apparatus 200 and then out of the aerosolizer 10 for patient inhalation.

During actuation, the aerosolizer 10 is adapted to experience significant pressure change. Particularly, pressurized liquid medicament 112 flow is created and passed through the transfusion apparatus/structure 200 in the direction of B to B'. Accordingly, the liquid medicament 112 travels from a high pressure end to a low pressure end of the aerosolizer 10. Moreover, at least during actuation, it is important that there is no leakage of the liquid medicament 112 aerosolizer. A leakage may cause pressure loss, which may further lead to decreased aerosolization efficiency, imprecise dosage delivery, clogging of the components, and reduced life of the aerosolizer. The present disclosure introduces a transfusion apparatus 200 with components having specific structure, characteristic and interactions thereof so as to avoid the foregoing issues.

Figure 3:
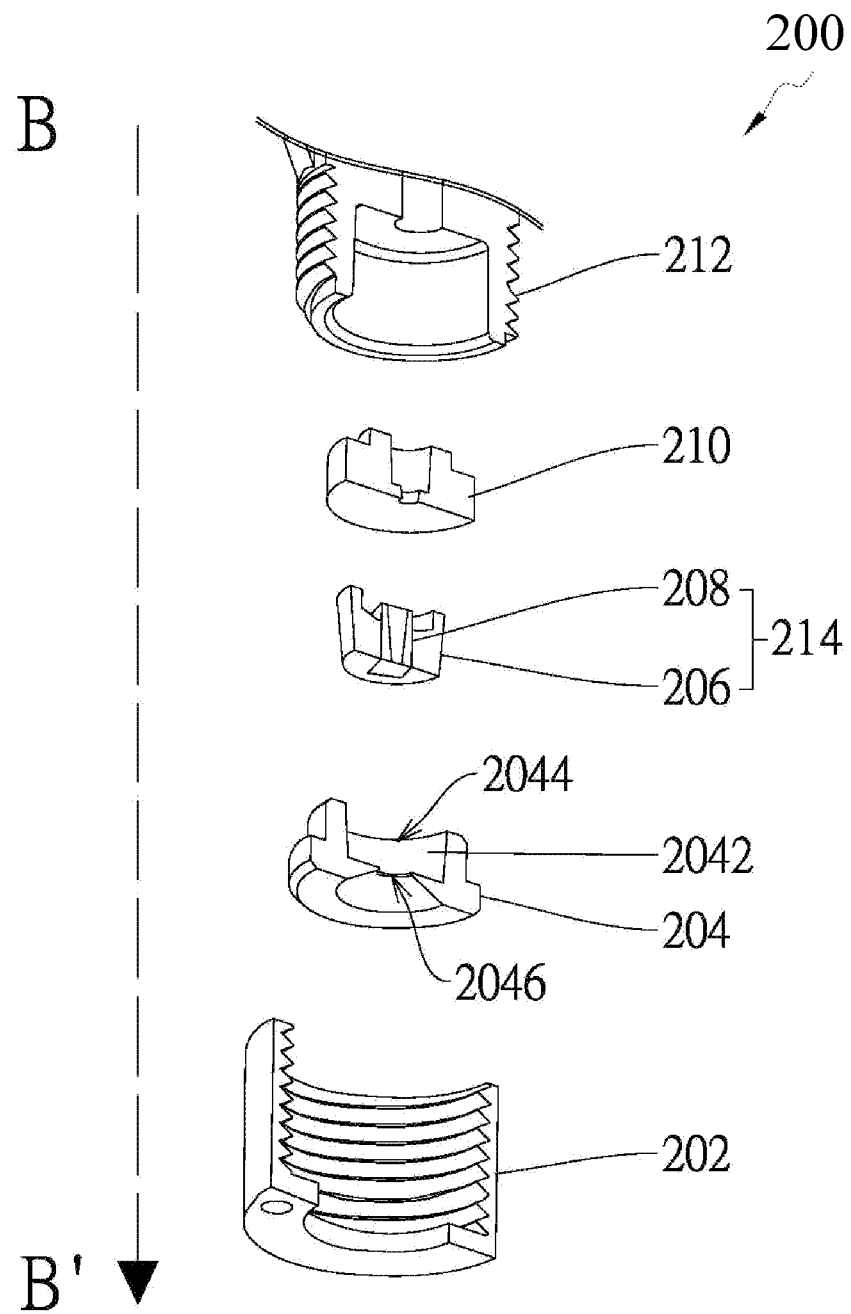
FIG. 3 is an exploded, cross-sectional view of the transfusion apparatus according to certain embodiments of the present disclosure.

Attention is now directed to FIG. 3, which is an exploded, cross-sectional view of the transfusion apparatus according to certain embodiments of the present disclosure. The transfusion apparatus 200 includes the following components: a check nut 202, a receptacle 204, an elastomeric ring 206, a nozzle 208, a cap 210, and a casing 212. The nozzle 208 is received by the elastomeric ring 206, and the combination thereof is sometimes referred to as a nozzle assembly 214. A proper seal is formed and maintained between the nozzle 208 and the elastomeric ring 206 to the extent that liquid medicament can't escape during aerosolizer actuation. The nozzle assembly 214 is received by the internal volume 2042 of the receptacle 204, which is then covered by a cap 210. The combined structure of the nozzle assembly 214, the receptacle 204 and the cap 210 is then disposed in the casing 212. A check nut 202 is engaged with the casing 212 so as to secure the components therein. As illustrated, corresponding screw threads may be provided at the check nut 202 and the casing 212 such that the two can be secured together. The check nut 202 and the casing 212 may be coupled by any other means known in the art.

Still at FIG. 3, liquid medicament (not shown) travels through the components of the transfusion apparatus 200 in the direction from B to B' for aerosolization. More particularly, the liquid medicament travels from a high pressure end and to a low pressure end of the nozzle assembly 214. Preferably, airtight seal is maintained between the components of the transfusion apparatus 200, and at least between the elastomeric ring 206 and the nozzle 208, and between the elastomeric ring 206 and the cap 210. Accordingly, no pressure loss or leakage occurs during actuation and the resulting aerosolization is controlled and precise. It is to be noted "no pressure loss" means no undesired or uncontrolled pressure loss, which may result in imprecise dosage and contamination to the aerosolizer. As the pressurized liquid medicament travels from a high pressure end to a lower pressure, there will be pressure decrease. However, such decrease will not affect the dosing accuracy of the nebulizer. In other words, such decrease is not equal to the "pressure loss", which leads to undesirable aerosolization effects, as used in the present disclosure. Furthermore, in certain embodiments, the "seal" (or "proper seal", as used throughout the present disclosure) between the components may be liquid tight seal. In a preferred embodiment, the seal is a vacuum or airtight seal. The present disclosure prevents leakage of the liquid medicament inside the aerosolizer, either during actuation or after extended use, through proper seal.

The receptacle 204 further includes an inlet opening 2044 and an outlet opening 2046. The inlet opening 2044 is at the relatively high pressure end and the outlet opening is at the relatively low pressure end of the receptacle 204, pursuant to the flow direction of the pressurized liquid medicament. Aerosol exits the receptacle 204 from the outlet opening 2046, which then leaves the aerosolizer for patient inhalation. As shown in FIG. 3, the receptacle 204 further includes a circular, widening wall such that aerosol travels out of the aerosolizer with lowered hindrance or blockage.

Figure 4:
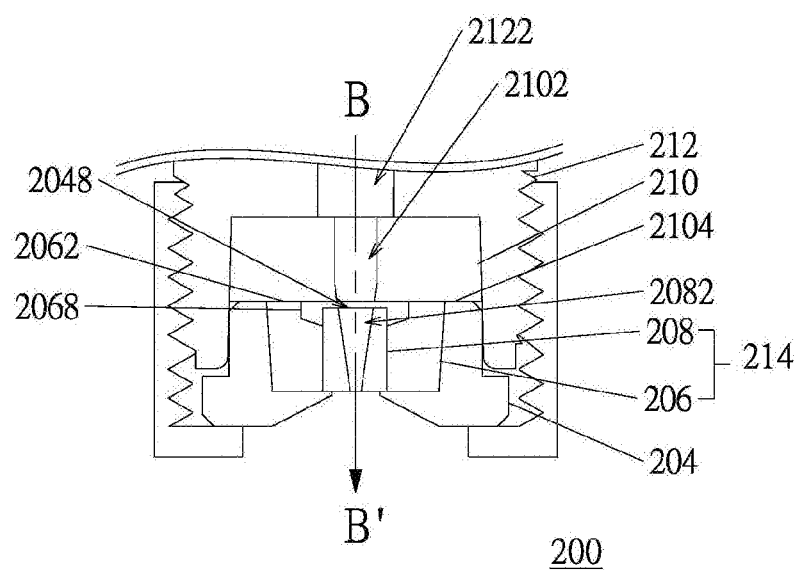
FIG. 4 is a cross-sectional view of the transfusion apparatus pursuant to some embodiments of the present disclosure.

FIG. 4 is a cross-sectional view of the transfusion apparatus 200 pursuant to some embodiments of the present disclosure. Liquid medicament (not shown) travels through the transfusion apparatus 200 in the direction from B to B', i.e., from a high pressure end to a low pressure end. The casing 212 includes a channel 2122 such that the liquid medicament can travel through. Correspondingly, the cap 210 includes a through hole 2102 such that liquid medicament can pass through and enter the internal volume 2042 of the receptacle 204 and thus the nozzle assembly 214.

The nozzle 208 may consist of glass and/or silicon materials. In one example, a silicon plate having microstructured channels is provided as a base. A cover is bonded to such base to form an enclosure, such that the nozzle 208 is assembled. The nozzle 208 includes a bore 2082, which corresponds to the aforementioned microstructured channels, such that the liquid medicament can travel through. The bore 2082 connects an inlet and the outlet of the nozzle 208, and the outlet opening thereof is about 5 micron to 12 micron in radius or width. Liquid medicament can only exit the nozzle 208 through the outlet opening when the aerosolizer is actuated. Also, the bore 2082 connects the inlet opening 2044 and the outlet opening 2046 of the receptacle 204. The nozzle 208 may be a rectangular structure having a width. Such width may be slightly larger or equal to the width of the internal contour of the elastomeric ring 206. Reasons for such configuration will be discussed later. The bore 2082 narrows in the direction from B to B' so as to facilitate aerosolization.

The elastomeric ring 206 is made of elastic material(s), including natural rubber or synthetic rubber such as silicon rubber. However, the foregoing shall not be limiting. Any flexible material known by a person having ordinary skill in the art is within the scope of this disclosure. Moreover, the compression set of the elastomeric ring 206 is between 5-30% and preferably between 10-20%. The relatively low compression set is preferred to maintain the shape of the elastomeric ring 206, which will reduce the chance of the elastomeric ring 206 being deformed in an undesirable manner. The foregoing better facilitates the seal needed.

The elastomeric ring 206 is configured to receive the nozzle 208, and its internal contour may be in direct contact with the outer perimeter of the nozzle 208. Again, proper seal is maintained between the elastomeric ring 206 and the nozzle 208 such that pressurized liquid medicament does not leak. The upper surface 2062 of the elastomeric ring 206 is in contact with the cap 210. Proper seal is also maintained therebetween so as to prevent leakage of the pressurized liquid medicament therefrom. The elastomeric ring 206 is accommodated by the receptacle 204. Along with the nozzle 208, the elastomeric ring 206 is secured within the internal volume 2042 by the receptacle 204 and the cap 210. Moreover, the elastomeric ring 206 and the nozzle 208 occupy a substantial part of the internal volume 2042 except for an unoccupied volume 2048 (or a void) corresponding to the inlet design of the elastomeric ring 206 and surrounding the inlet end of the nozzle 208. Alternatively, there might be other gap or dead volume not occupied by the elastomeric ring 206 as long as the proper seal is not compromised. As such, part of the outer perimeter of the nozzle 208 is not in contact with the elastomeric ring 206. Still, the unoccupied volume 2048 will not affect the seal between the elastomeric ring 206 and the nozzle 208. In fact, it is the result of the specific structural design (an inclined surface 2068 at the liquid inlet end) of the elastomeric ring 206. Furthermore, such design of the unoccupied volume 2048 may be served as a buffer before each actuation for the pressurized liquid medicament while dosing accuracy is not affected. In certain embodiments, the unoccupied volume accounts about 0.29 mm3 of space, which accounts for about 0.8% to 1.2%, and preferably about 1%, and more precisely about 1.06% of the internal volume 2042. In any event, the void shall not account for more than 2% of the internal volume 2042 such that dosing accuracy may not be affected. In certain embodiments, the unoccupied volume 2048 is U-shaped or substantially U-shaped. Still, the unoccupied volume 2048 may be any shape corresponding to the internal contour of the elastomeric ring 206. Moreover, due to the design of such unoccupied volume 2048, a contacting area between the elastomeric ring 206 and the outer perimeter of the nozzle 208 is smaller than the contacting area between the elastomeric ring 206 and an inner wall of the receptacle 204.

The cap 210 includes an entirely flat surface 2104 facing the elastomeric ring 206. When assembled, the surface 2104 is in contact with the upper surface of the receptacle 204 and the upper surface of the elastomeric ring 206. No part of the cap 210 is extended into the internal volume 2042. When the check nut 202 and the casing 212 are coupled, the cap 210 is further pressed towards the receptacle 204 to improve the seal between the elastomeric ring 206, the nozzle 208 and the cap 210. Vacuum tight is preferred such that chance of pressurized liquid medicament leakage in the transfusion apparatus 200 is reduced. In other words, once the transfusion apparatus 200 is assembled, pressurized liquid medicament should only exit through the outlet opening 2046 and nowhere else. Therefore, a level of seal that is at minimum liquid tight is desired to achieve the functionality of the aerosolizer of the present disclosure. Vacuum or airtight seal may be further configured via additional processing or treatment to certain components of the transfusion apparatus 200.

It is important to note that throughout the entire disclosure, the definition of "in contact" should not be limited to "in direct contact" unless otherwise specified. For example, "in contact" may include circumstances that certain material(s) is provided between such components.

As proper seal is maintained between the components of the transfusion apparatus 200, pressurized liquid medicament may be more accurately directed in the direction from B to B' in a controlled manner. If such seal is compromised, liquid medicament may leak inside the transfusion apparatus 200. This may cause malfunction and damage to the aerosolizer 10, affecting its efficiency and life. In other words, the interior of the aerosolizer is preferably isolated from the outside environment such that contamination may be avoided and dosing accuracy may be increased. In another example, liquid medicament leaked out of the aerosolizer 10 may contaminate the aerosolizer itself or the liquid medicament still in the storage container 108. In another aspect, proper seal further serves to ensure that a fixed, precise amount of liquid medicament is aerosolized and delivered out of the outlet opening 2046 in each actuation.

Figure 5A:
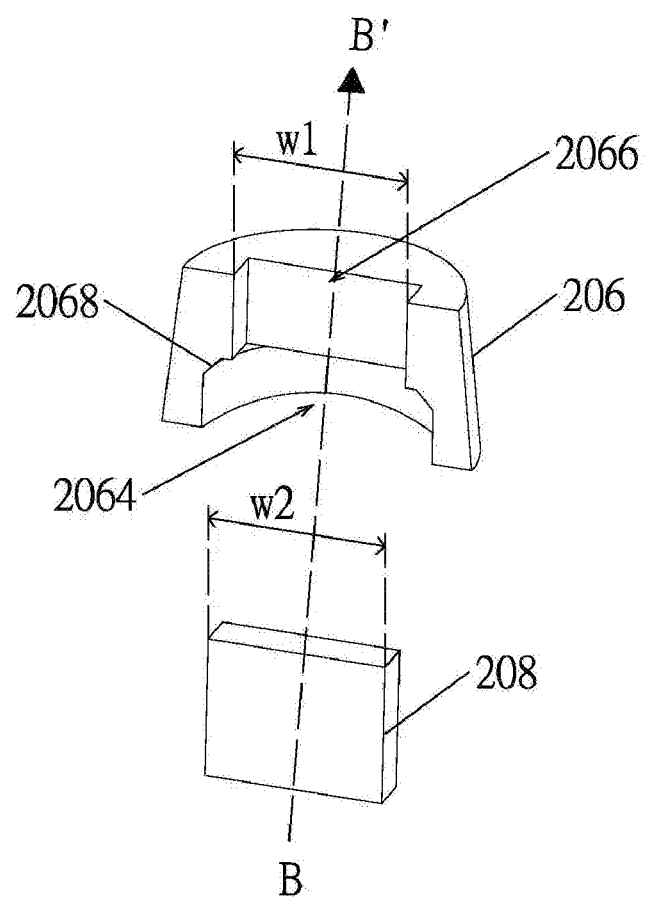
FIGS. 5A to 5C are cross-sectional views of the elastomeric ring and the nozzle pursuant to some embodiments of the present disclosure.
Figure 5B:
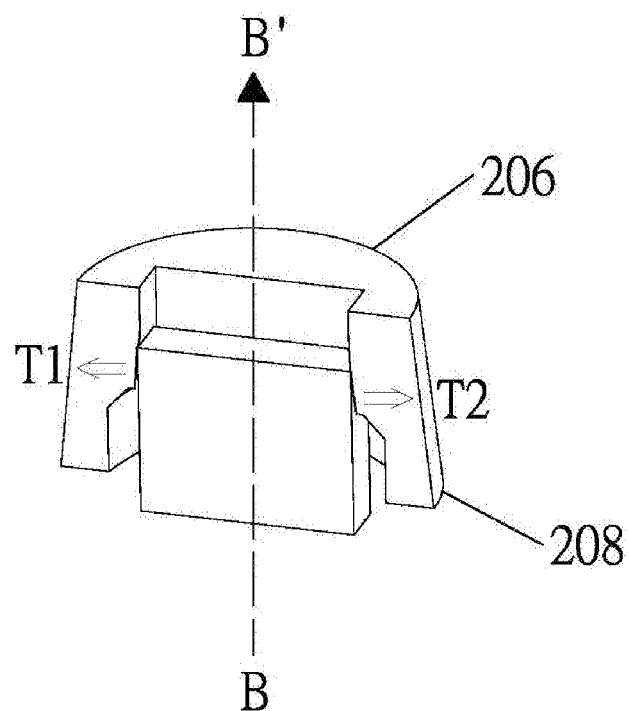
Figure 5C:
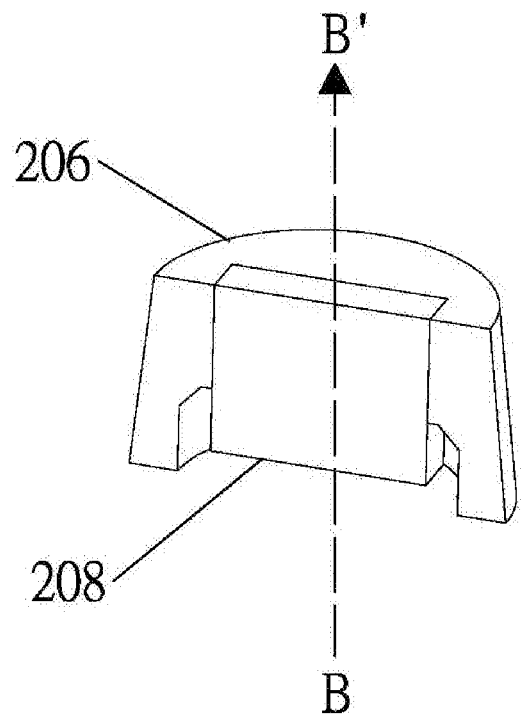

FIGS. 5A to 5C are cross-sectional views of the elastomeric ring and the nozzle pursuant to some embodiments of the present disclosure. Again, certain details of the components are omitted for easy illustration and explanation purposes. Scales thereof are also adjusted, and some exaggerated, for the same purposes. The foregoing shall not be considered as limiting whatsoever.

In FIG. 5A, as discussed, the nozzle 208 may be a rectangular structure having a width w2. The elastomeric ring 206 includes an internal contour also of a rectangular shape having a width w1. The width w2 is larger than the width w1 to improve the seal between the elastomeric ring 206 and the nozzle 208. The width w2 may be only slightly larger than w1. In some embodiments, the difference therebetween is about 0.1 mm, which may not be readily visible to human eyes. Due to the flexibility of the elastomeric ring 206, it can be stretched if force is applied. For example, with reference to FIG. 5B, when the nozzle 208 is shoved into the elastomeric ring 206, the internal contour of the elastomeric ring 206 may stretch and expand to accommodate the nozzle 208 such that the width w1 is increased to at least the same as or slightly more than w2. More specifically, the internal contour of the elastomeric ring 206 is stretched/tensioned along direction (as indicated by the arrows T1 and T2) perpendicular to the direction from B to B'. In certain embodiments, the elastomeric ring 206 includes an inlet 2064 and an outlet 2066, and the elastomeric ring 206 is stretched and expanded along directions perpendicular to that from the inlet to the outlet. As such, the nozzle 208 can be forced into the elastomeric ring 206 even when width w2 is larger than w1.

With reference to FIG. 5C, the internal contour of the elastomeric ring 206 firmly accommodates the nozzle 208. Specifically, the elastic nature of elastomeric ring 206 allows the elastomeric ring 206 to stretch and then clamp the nozzle 208 after it resumes to its former shape, although may not be entirely. The reforming force is one of the methods to generate a proper seal between the elastomeric ring 206 and the nozzle 208 as disclosed by the present disclosure. For example, a desirable alignment between the contacting surfaces of the elastomeric ring 206 and the nozzle 208 may be achieved. Still, in yet some other embodiments, the width w1 may be equal to w2 and the nozzle 208 may be slipped into the elastomeric ring 206 without deforming it.

FIGS. 6A to 6D are a cross-sectional views of the nozzle assembly and the receptacle pursuant to some embodiments of the present disclosure.

Figure 6A:
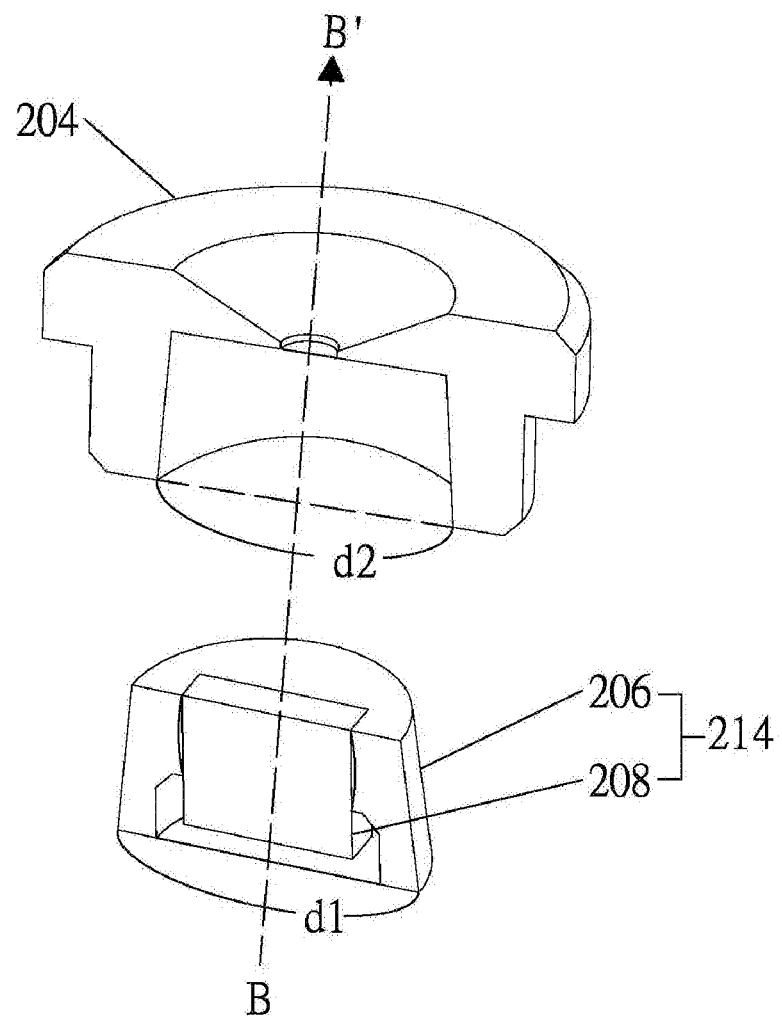
FIGS. 6A to 6D are cross-sectional views of the nozzle assembly and the receptacle pursuant to some embodiments of the present disclosure.
Figure 6B:
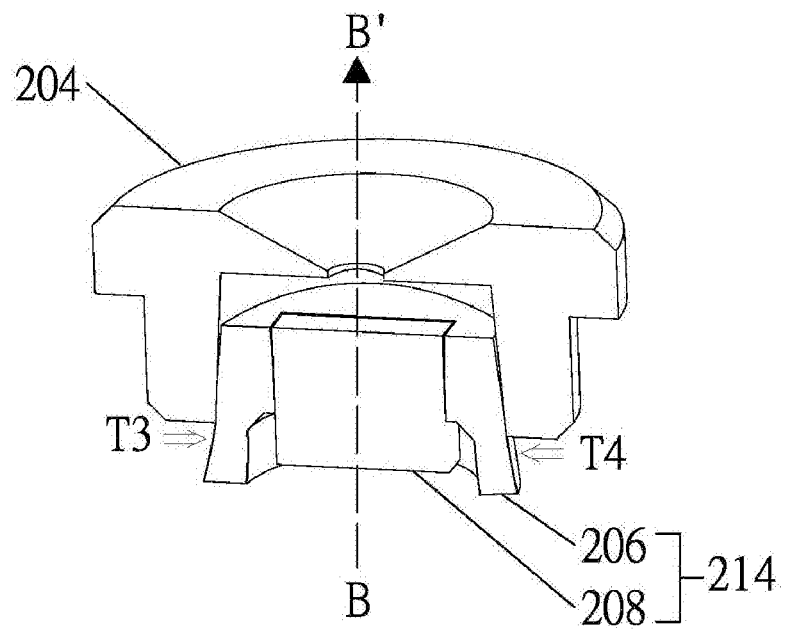

Referring to FIG. 6A, a dimension of the nozzle assembly 214 is at least slightly larger than that of the internal volume 2042 of the receptacle 204. For example, a diameter d1 of the outer contour of the elastomeric ring 206 of the nozzle assembly 214 is larger than an internal diameter d2 of the receptacle 204 by 0.1 mm to 0.2 mm. As such, to insert or shove the nozzle assembly 214 into the receptacle 204, the elastomeric ring 206 will be compressed and deformed. With reference to FIG. 6B, the elastomeric ring 206 is compressed (or over-tensioned) such that it can be squeezed into the receptacle 204. More specifically, the outer wall of the elastomeric ring 206 is compressed along directions (as indicated by the arrows T3 and T4) perpendicular to the direction from B to B'. As such, the nozzle assembly 214 can be inserted into the receptacle 204 even with a diameter d1 larger than d2. This may also result in a slight shape change of the internal wall of the elastomeric ring 206. The foregoing serves to form a better alignment between the contacting surfaces of the elastomeric ring 206 and the receptacle 204, thus improving the seal.

Figure 6C:
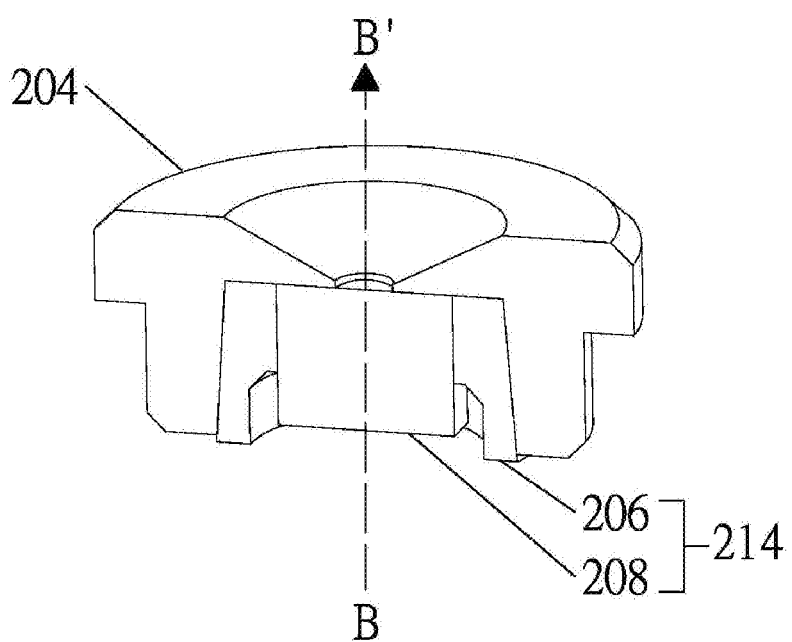

FIG. 6C shows a completed assembly of the nozzle assembly 214 and the receptacle 204. At this stage, although not shown by the figures, the elastomeric ring 206 may resume to its former shape to a certain degree. Such reformation serves to ensure a proper seal between the elastomeric ring 206 and the nozzle 208, and the elastomeric ring 206 and the receptacle 204. The resulting structure may be more suitable to function under high pressured environment, which is required during the actuation of the aerosolizer 10.

Figure 6D:
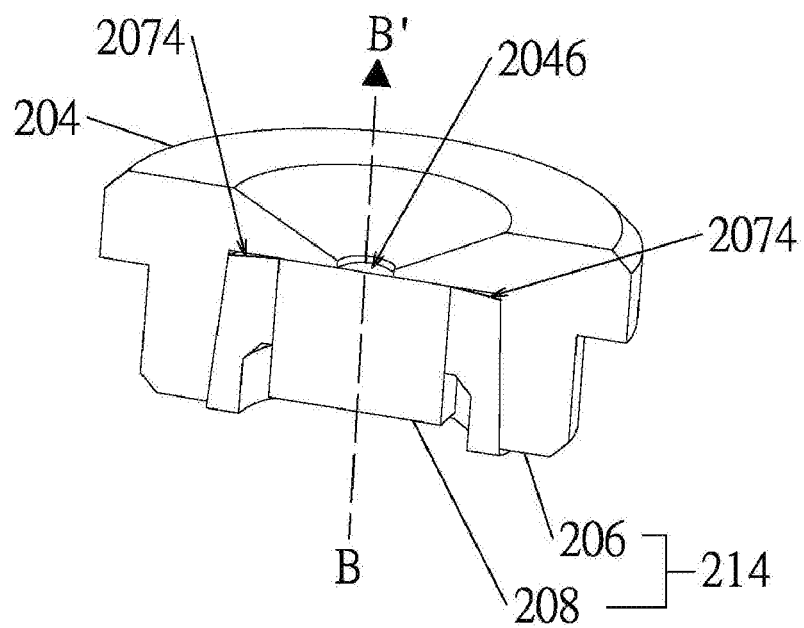

With reference to FIG. 6D, another exemplary embodiment of the nozzle assembly 214 and the receptacle 204 is disclosed. Here, the elastomeric ring 206 includes an inclined surface 2074 facing the outlet opening 2046 end of the receptacle 204. Accordingly, a gap is formed therebetween. The gap serves as a buffer for the movement and/or deformation of the elastomeric ring 206 resulting from the passing of the pressurized liquid. As a result, the proper seal is achieved. Without such gap, the seal might be compromised after prolonged use due to damage to or fatigue of the elastomeric ring 206.

Figure 7A:
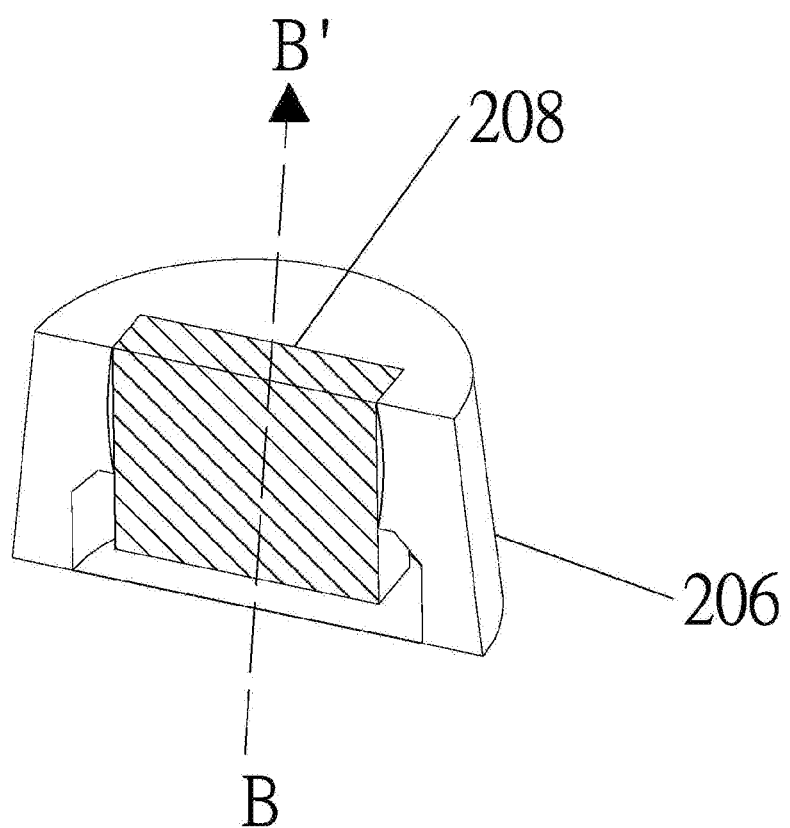
FIGS. 7A to 7C are cross-sectional views of the elastomeric ring and the nozzle pursuant to some embodiments of the present disclosure.
Figure 7B:
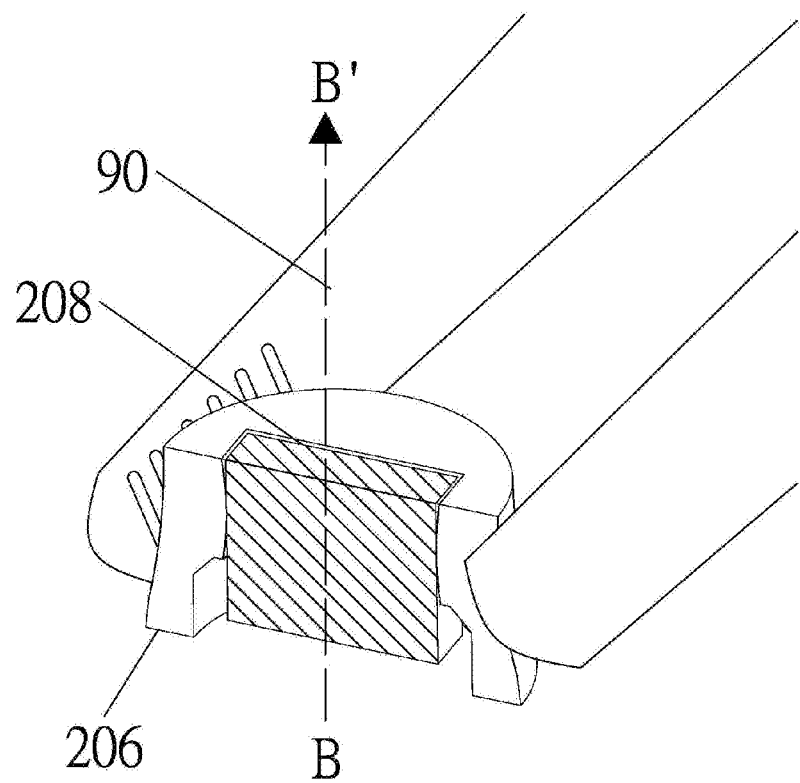
Figure 7C:
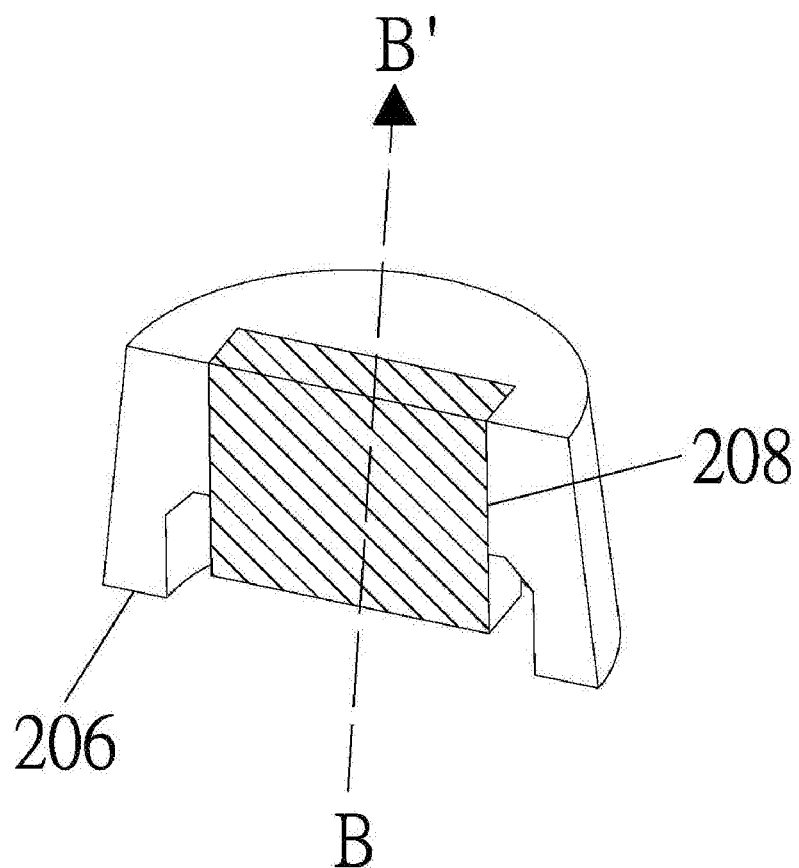

FIGS. 7A to 7C are cross-sectional views of the elastomeric ring and the nozzle pursuant to some embodiments of the present disclosure.

In FIG. 7A, the nozzle 208 has been inserted into the elastomeric ring 206. Corresponding ends of the nozzle 208 and the elastomeric ring 206 are aligned. As illustrated, certain space or void may still exist therebetween due to, e.g., manufacture tolerance of the components. Air needs to be vacuumed from such space to achieve proper seal. One way to achieve the foregoing is to apply force to the elastomeric ring 206, as shown in FIG. 7B. Here, as an example, a clamping device 90 is used to squeeze the elastomeric ring 206 towards its center. As a result, any void between the nozzle 208 and the elastomeric ring 206 may be removed and a proper seal is created, as show in FIG. 7C. In certain embodiments, the inward, squeezing force is to be applied for a prolonged period to ensure that the elastomeric ring 206 won't return to its previous shape to reopen the void. In some other embodiments, a processing or treatment can be applied to the elastomeric ring 206 and/or the nozzle 208 such that a seal is better formed and preserved. Additional interface layer(s) may also be applied such that air is expelled from between the elastomeric ring 206 and the nozzle 208, and a vacuum may be considered formed.

In certain embodiments, the contacting surfaces between the elastomeric ring 206 and/or the nozzle 208 may be processed, during or post manufacture, so as to reach a predetermined static friction therebetween, of at least 4 newton and preferably at least 11 newton, to achieve proper seal. For example, such contacting surfaces may be polished to be uniformly smooth. An exceptionally smooth surface serves to increase the contact area between the surfaces, hence leads to reduced void or space therebetween. In certain embodiments, the friction between the nozzle 208 and the elastomeric ring 206 may be further increased such that the stability of the nozzle assembly 214 is enhanced, especially after prolonged use. For example, larger friction therebetween means less likelihood of the nozzle 208 being moved relative to the elastomeric ring 206 during actuation. The maintenance of such position may serve to increase the life and dosing accuracy of the aerosolizer because the elastomeric ring 206 and the nozzle 208 are less prone to damage from movement due to actuation. Pressure stability may also be better maintained if proper seal is achieved. In certain embodiments, at least the internal contour of the elastomeric ring 206 and the surface of the outer perimeter of the nozzle 208 has an average peak-valley distance difference between about 0.019 and 0.12 micron, and preferably between about 0.019 and 0.06 micron. According to certain embodiments, the smoothness of the elastomeric ring 206 and/or the nozzle 208 in the present disclosure is at least at the sand paper polishing level and preferably at the diamond polishing level.

There are still other ways to improve the seal between the elastomeric ring 206 and the nozzle 208. For example, an interface layer of material may be applied therebetween. The interface layer may be a liquid, an adhesive, or anything hydrophobic. The introduction of such interface layer may also improve seal.

There are yet other ways to improve the seal between the elastomeric ring 206 and the nozzle 208. For example, the elastomeric ring 206 may be treated with plasma such that the surface thereof becomes hydrophilic. Thereafter, the nozzle 208 is inserted and force and heat are applied such that a hydrogen bond is created therebetween. The resulting nozzle assembly may result in stronger seal. In sum, the present disclosure teaches that any friction-increasing or void-decreasing treatment may be applied to the internal contour of the elastomeric ring 206 as long as a resulting static friction between the elastomeric ring 206 and the nozzle 208 is at least 4 newton and preferably 11 newton. The foregoing is ideal for liquid transfusion components working in the high-pressured environment to prevent leakage and pressure loss.

Figure 8A:
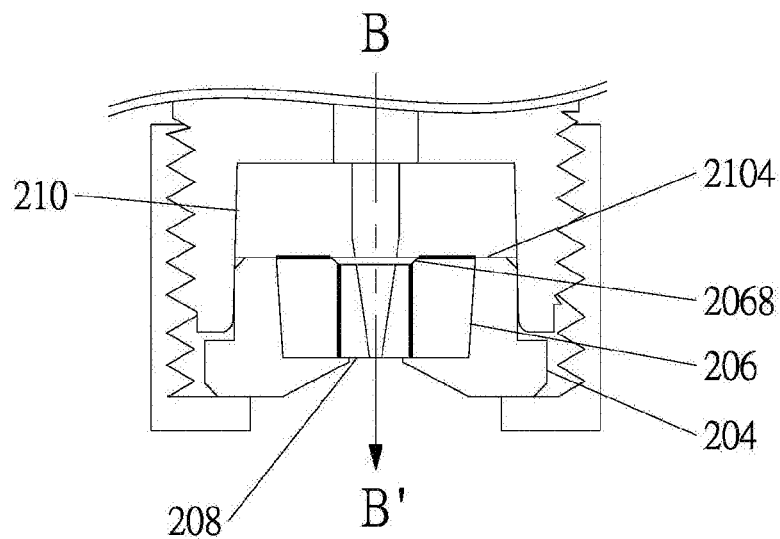
FIGS. 8A and 8B are a cross-sectional views of the transfusion apparatus pursuant to the present disclosure.
Figure 8B:
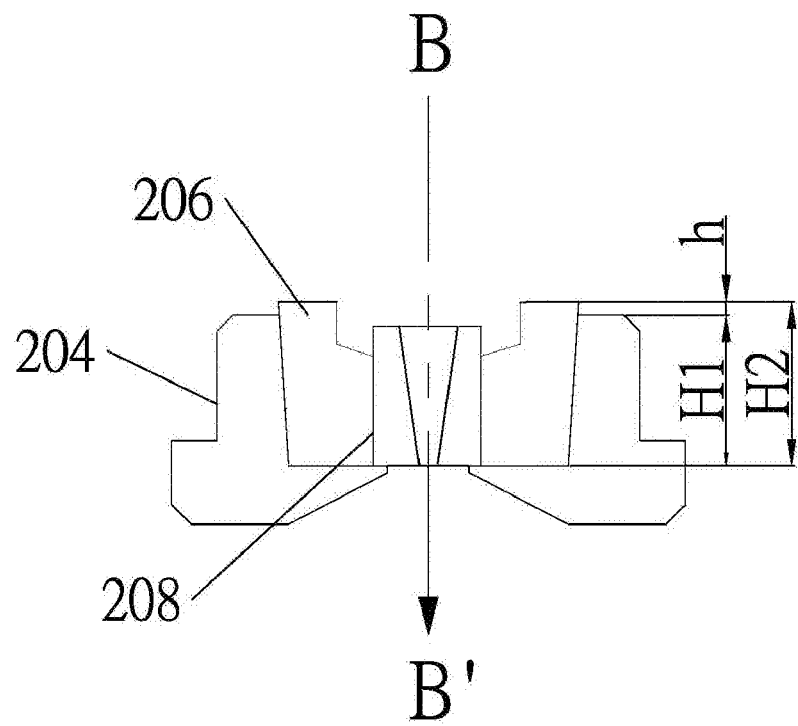

FIGS. 8A-8B are a cross-sectional views of the transfusion apparatus 200 pursuant to the present disclosure.

With reference to FIG. 8A, in some embodiments, portions of the elastomeric ring 206 is processed or applied with treatment such that proper seal can be achieved. In one example, the entire elastomeric ring 206 may be processed. Alternatively, only part of the elastomeric ring 206 is processed. Moreover, the elastomeric ring 206 may be pre-processed during manufacture or subject to process post manufacture.

Still at FIG. 8A, as indicated by the boldface highlight (hereinafter "contacting surfaces"), the elastomeric ring 206 is processed at its internal contour and its upper surface facing the cap 210 pursuant to certain embodiments. Accordingly, sections of the processed elastomeric ring 206 are in contact with a portion of the cap 210 and a portion of the outer perimeter of the nozzle 208. Such contacting surfaces may result in seals between the elastomeric ring 206, the nozzle 208 and the cap 210. It is to be again noted that the thickness of the contacting surfaces is exaggerated (boldface highlight) for purposes of explaining the present disclosure, and should not be considered as limiting.

A fixed amount, e.g., single dosage, of liquid medicament can be directed to enter the nozzle 208 for aerosolization. The resulting aerosol can then leave via the outlet opening of the nozzle and the outlet opening 2046 of the receptacle 204. Precise dosage control is achieved. Proper seal would prevent the liquid medicament from escaping, thereby reduce residue built up on the components of the aerosolizer 10. Chances of contamination of the aerosolizer 10 is also lowered, hence the life of the aerosolizer 10 may be prolonged.

Still referring to FIG. 8A, as discussed, the surface 2104 of the cap 210 facing the receptacle 204 is continuously flat. Such surface 2104 is also where the cap 210 contacts the upper surface of the elastomeric ring 206, which might be processed and/or flat. It is important to note that because the surface 2104 is entirely and continuously flat, no part of the cap 210 extends into the internal volume of the receptacle 204. When the casing 212 and the check nut 202 are engaged, the elastomeric ring 206 is equal in height with that of the receptacle 204. More particularly, when the cap 210 is engaged with the receptacle 204, the cap 210 would refrain from deforming the elastomeric ring 206 while creating a seal therebetween. In other words, the height of the elastomeric ring 206 is identical to the height of the internal wall of the receptacle 204. Furthermore, in certain embodiments, an annular gasket (not shown) may be added in-between the receptacle 204 and the cap 210. Particularly, the gasket is in contact with both the surface 2104 and upper portions (either processed and/or flat) of the elastomeric ring 206 to further improve the seal. The gasket may be made from rubber or materials having similar characteristic. In some embodiments, the combined height of the gasket and the elastomeric ring 206 after the cap 210 is engaged with the receptacle 204 is equal to the height of the receptacle 204.

Alternatively, in another embodiment, the height of the elastomeric ring 206 may be larger than the height of the internal wall of the receptacle 204 but not to a substantial extent, as depicted in FIG. 8B. Therefore, when the casing 212 and the check nut 202 are engaged, the elastomeric ring 206 is slightly pressed and deformed by the cap 210 while a proper seal therebetween is formed. Here, the elastomeric ring 206 may resume to its original shape if the force applied by the cap 210 is removed.

Still at FIG. 8B, as depicted, in a preferred embodiment, elastomeric ring 206 has a height of H2, the internal wall of the receptacle 204 has a height of H1, and the difference thereof is h. In other words, the elastomeric ring 206 is slightly higher than the receptacle 204 by a height h. Therefore, when being assembled, the cap (not shown) is pressed towards and compresses the elastomeric ring 206, and such height h is diminished. The height h should be no more than 35% of the height H2, and more preferable between about 10% to 20% such that a proper seal is formed post assembly. The aforementioned range can also be understood as that the height is greater than the tolerance of the elastomeric ring 206, which is about 0.1 mm, so as to facilitate the proper seal. Moreover, again, the elastomeric ring 206 has a compression set between 5-30% and preferably between 10-20%. The preferred lower compression set means the chance of the elastomeric ring 206 being further deformed is lowered. For example, if the compressed set is about 10%, the elastomeric ring 206 may at most have an additional 10% of deformation in addition to the height h. The foregoing increases the formation of the proper seal needed. Such preferred lower compression set may further maintain the proper seal after prolonged use of the aerosolizer. In addition, the hardness of the elastomeric ring 206 is at least 70%, and preferably 80-90%. For example, with an elastomeric ring 206 of a higher hardness, its original shape is better maintained and undesired deformation may be avoided. As such, the elastomeric ring 206 can better maintain the position of the nozzle 208 during actuation after prolonged use under high pressured environment (for example, a pressurized fluid passing through with at least 130 bar, and preferably between about 130 bar to 250 bar). A lower hardness may result in undesirable deformation or permanent shape change, thus causing damage to the elastomeric ring 206. The foregoing might decrease the structural integrity and life of the aerosolizer.

Assembly Method

FIGS. 9A-9I illustrates a method for assembling the transfusion apparatus according to certain embodiments of the present disclosure.

Figure 9A:
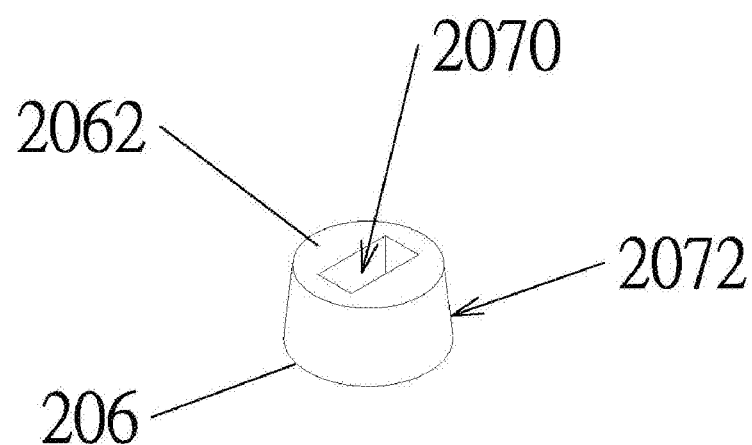
FIGS. 9A-9I illustrates a method for manufacturing the transfusion apparatus according to certain embodiments of the present disclosure.

With reference to FIG. 9A, in one step, an elastomeric ring 206 is prepared. The elastomeric ring 206 may be manufactured by injection molding, and the mold may be specifically configured to give the resulting elastomeric ring certain characteristics. For example, the elastomeric ring 206 may be smooth to a sand paper level or up to a diamond level. Here, the elastomeric ring 206 includes two opposite ends, and one of the ends includes the upper surface 2062 later facing the receptacle (not shown). Connecting the two ends is a through hole 2070 defined by an internal contour. The elastomeric ring also includes an outer contour defined by its outer wall 2072.

Figure 9B:
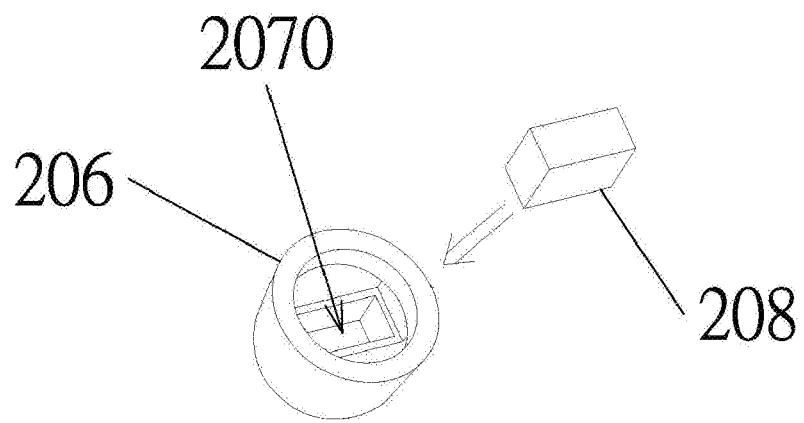
Figure 9C:
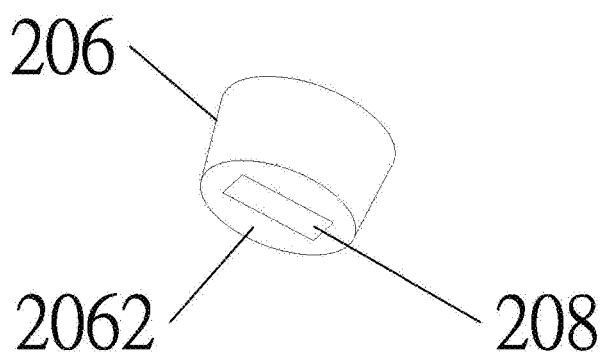
Figure 9C:
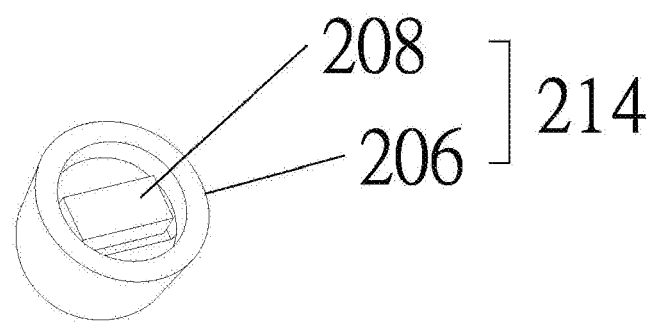

With reference to FIG. 9B, in one step, a nozzle 208 is to be inserted into the elastomeric ring 206. With reference to FIG. 5B, the internal contour of the elastomeric ring 206 would stretch and expand to such an extent to receive the nozzle 208. Relevant operations thereof have been disclosed in FIG. 5B and the relevant paragraphs, and will not be repeated. The nozzle 208 continues to move forward within the elastomeric ring 206 until it is aligned with one end of the elastomeric ring 206. In the embodiment shown by FIG. 9C, the nozzle 208 is aligned with the upper surface 2062. As such, a nozzle assembly 214 is assembled.

Figure 9D:
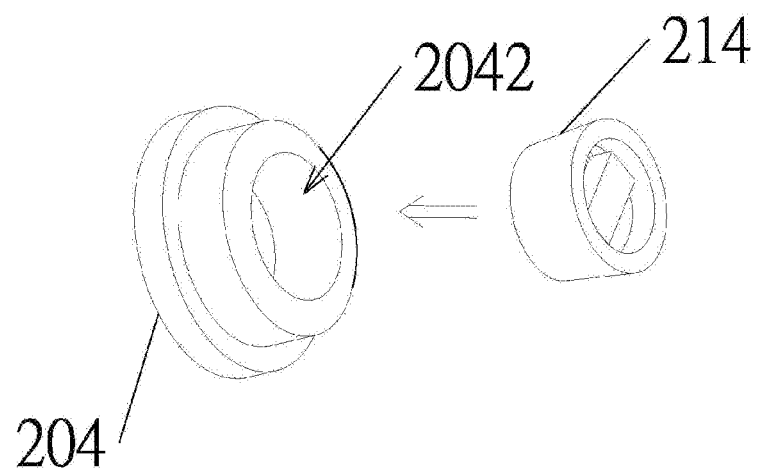
Figure 9E:
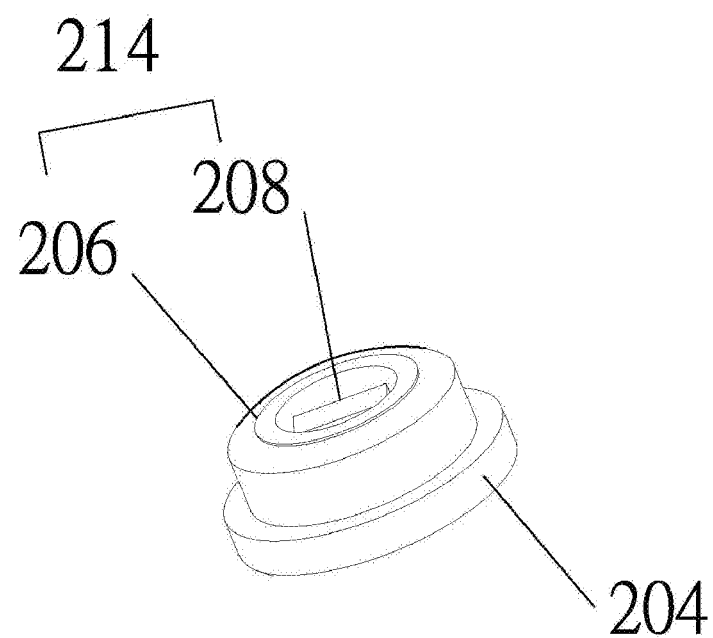

With reference to FIG. 9D, in one step, a receptacle 204 is provided for receiving the nozzle assembly 214. With reference to FIG. 6B, force is applied to compress the elastomeric ring 206 such that the nozzle assembly 214 may fit into the internal volume 2042 of the receptacle 204. As discussed in FIG. 6B relevant disclosure, the outer contour of the elastomeric ring 206 is deformed so as to decrease its diameter. The nozzle assembly 214 continues to be pushed into the internal volume 2042 until it's entirely received by the receptacle 204, as show in FIG. 9E.

Figure 9F:
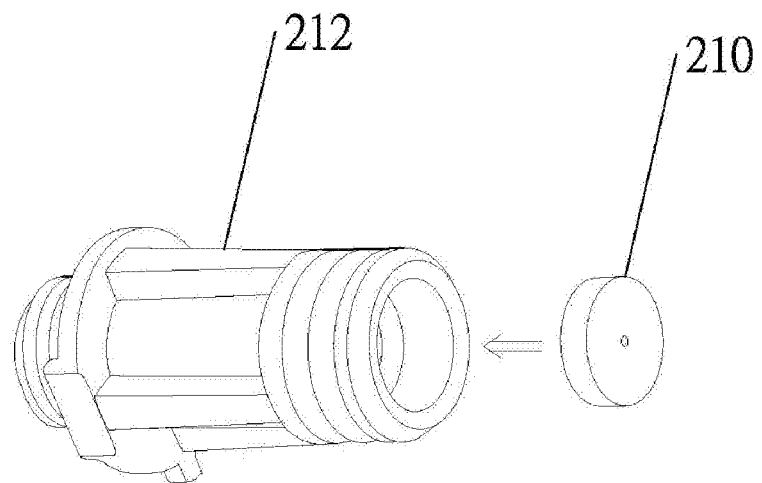
Figure 9G:
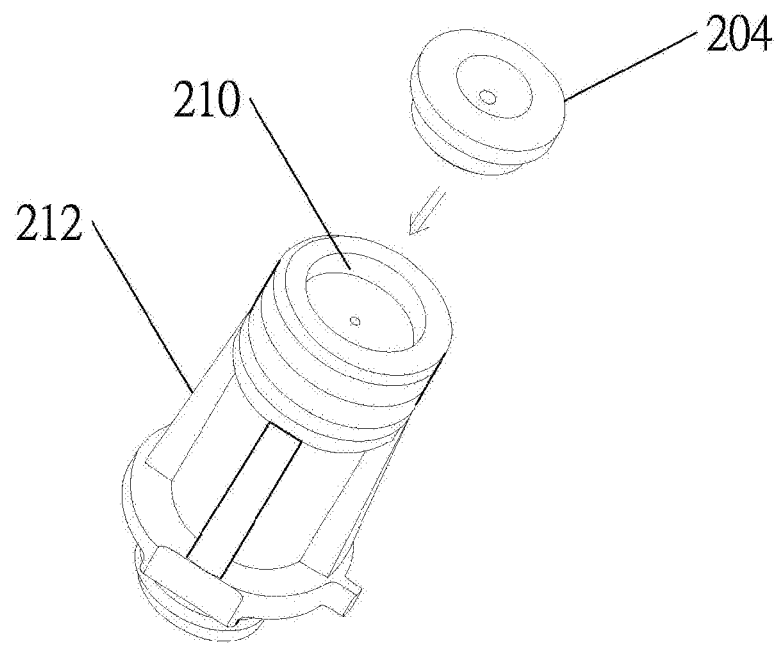

With reference to FIG. 9F, in one step, a casing 212 and a cap 210 are provided. The cap 210 having an entirely flat surface is disposed into the casing 212 for later use. In certain embodiments, the cap 210 may be coupled with the nozzle assembly 214 first before being adapted into the casing 212. A persona having ordinary skill in the art would understand that there is no specific ordering regarding the assembly of the aforementioned components, as long as a proper seal can be formed. With reference to FIG. 9G, in one step, at least part of the receptacle 204 with the nozzle assembly (obstructed, not shown) is inserted into the casing 212. As such, the cap 210 now covers the inlet opening of the receptacle 204 such that the nozzle assembly can be encased therein.

Figure 9H:
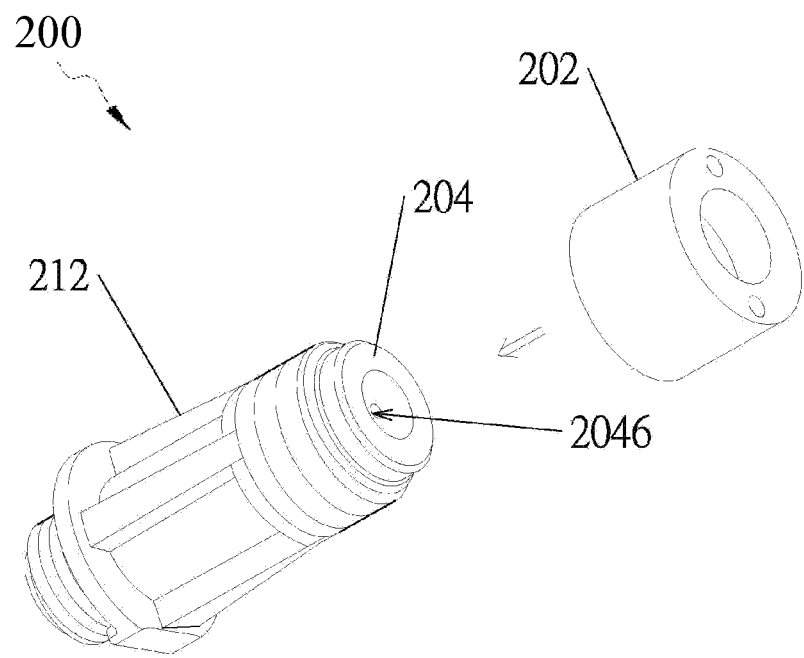
Figure 9I:
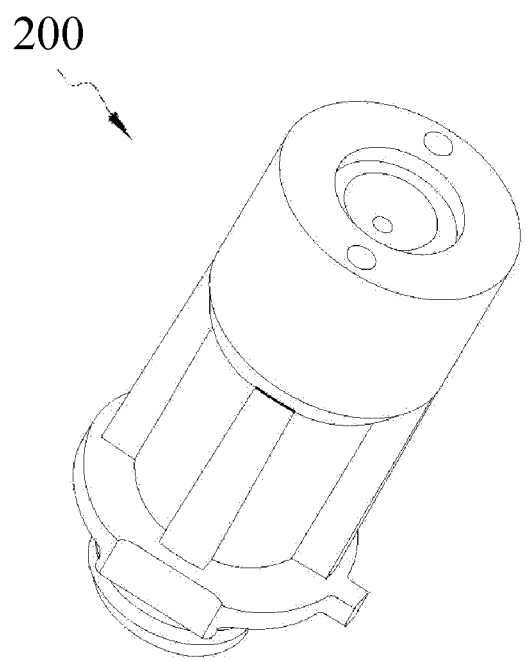

With reference to FIG. 9H, in one step, a check nut 202 is engaged with the casing 212 so as to secure the components therein. Such engagement also serves to push the cap towards the receptacle and the nozzle assembly therein so as to improve the seal required by the aerosolizer of the present disclosure. Now, the assembly of the transfusion apparatus 200 is complete. With reference to FIG. 9I and FIG. 2, the assembled transfusion apparatus 200 is to be coupled with certain other components to form a functional aerosolizer 10. Pressurized liquid medicament is directed in the direction from B to B' to pass through the nozzle assembly 214 so as to be aerosolized. Due to the specific design and interaction of the components as disclosed in the present disclosure, leakage of the liquid medicament can be prevented. The aerosolizer 10 can provide precise dosage in each actuation and simplified components increase manufacturing efficiency.

In certain embodiments, the insertion of the nozzle 208 into the elastomeric ring 206 may be a two-step procedure. The nozzle 208 may be inserted into and moved along the elastomeric ring 206 to the extent that the nozzle 208 extends out at one end of the elastomeric ring 206. An opposite movement is then needed to push the nozzle 208 back into the elastomeric ring 206 until they are aligned. The foregoing might be ideal for manual assembly.

In certain embodiments, in one step, the internal diameter and the external radius of the elastomeric ring 206 is stretched/increased so as to fit the nozzle 208 and facilitate proper seal. The foregoing arises from the flexibility of the elastomeric ring 206. The resulting increase of the diameter/radius may serve to enhance the seal between the elastomeric ring 206 and the receptacle 204 post assembly. It is important to note that such dimension increase might not be linear and might not be visible to human eyes. The foregoing characteristic also applies to the decrease in diameter/radius when the nozzle assembly 214 is applied with force and pushed into the receptacle 204. In some embodiments, in one step, the dimension of the elastomeric ring 206 of the nozzle assembly 214 is adjusted to be adapted into the internal volume 2042 of the receptacle 204. For example, force may be applied so as to compress the elastomeric ring 206. The diameter of the elastomeric ring 206 may be decreased such that it may fit into the receptacle 204. As discussed in the previous paragraphs, the elastomeric ring 206 is deformable with a compression set between 5-30% and preferably between 10-20%. Accordingly, the elastomeric ring 206 may return to its original shape, although not entirely, if force/pressure is removed but not to the extent to its original shape/dimension entirely. That is, the diameter of the elastomeric ring 206 when the nozzle assembly 214 is received by the receptacle 204 is smaller than: (i) the diameter of the elastomeric ring 206 before the nozzle assembly 214 is received by the receptacle 204; and (ii) the diameter of the elastomeric ring 206 after the nozzle assembly 214 is removed from the receptacle 204.

In some embodiments, in one step, processing can be applied to the elastomeric ring 206 so as to change its physical or chemical property. It is important to note that such "processing" may be physical or chemical, and it may be applied during manufacture of the elastomeric ring 206. In other words, the elastomeric ring 206 may come with certain desired characteristic from its manufacturing process. The entire elastomeric ring 206 may be processed. Alternatively, only portions to be in contact with the cap 210 or the nozzle 208 are processed. In certain embodiments, processing is deliberately applied such that the surface of the internal contour and external contour of the elastomeric ring 206 is different.

The processing is applied to increase friction between the elastomeric ring 206 and a contacting area with another object. For example, when friction is increased between the elastomeric ring 206 and the nozzle 208, the combination thereof is capable of withstanding heightened liquid pressure without breakage or leakage therebetween. In some embodiments, seal between the elastomeric ring 206 and the nozzle 208 may be improved by polishing their surfaces to be uniformly smooth in a micrometer scale. The foregoing can be understood as to adjust the smoothness of the elastomeric ring 206 or the nozzle 208. As a result, a static friction of at least 4 newton is generated between the elastomeric ring 206 and the nozzle 208. The foregoing static friction facilitates a stronger seal therebetween. The aforementioned processing may be applied to the elastomeric ring 206 and the nozzle 208 by means and machineries known by person having ordinary skill in the art.

In certain embodiments, in one step, material(s) may be applied to the surface of the elastomeric ring 206 and/or the nozzle 208 by spraying, smearing, dipping or any proper means. Such material is intended to stay on their surface so as to form an interface layer. The material may be applied to the elastomeric ring 206 and/or the nozzle 208 entirely, or only to certain portions thereof. For example, only such portions to be in contact with the nozzle is applied with a material. The application of the material serves to increase friction and/or facilitate seal between the elastomeric ring 206 and the nozzle 208. Adhesive may be used. However, it might complicate the assembly process. The material serves as an adherence-enhancing layer between the elastomeric ring 206 and the nozzle 208 such that at least 11 newton of force is needed to remove the nozzle from the elastomeric ring. It can be considered as a static friction of 11 newton exists between the elastomeric ring 206 and the nozzle 208 due to the application of the interface material. The elastomeric ring 206 and the nozzle 208 should still be able to be removed from each other without breakage such that assembly easiness is preserved.

In some embodiments, in one step, a material, such as solution, having hydrophobicity is applied. After the elastomeric ring 206 receives the nozzle 208, a force is applied (exemplary method illustrated in FIG. 7B) to expel air and create a vacuum seal therebetween. Consequently, contacting area between the elastomeric ring 206 and the nozzle 208 is increased, thus is the friction. The hydrophobic material may help to facilitate the air expelling. It is to be noted that ways for applying force is not limited to the disclosure in FIG. 7B. For example, in mass production, automated equipment or assembly line may be used.

In certain embodiments, in one step, a wetting process is applied to the elastomeric ring 206. For example, an agent may be applied to the elastomeric ring 206 such that intermolecular interaction is created/enhanced between the elastomeric ring 206 and the nozzle 208 and/or the cap 210. The wetting process also results in an interface layer of the wetting material formed therebetween. Again, with reference to FIG. 7B, force may be applied to expel air and create a vacuum. An exemplary way to apply force is to clamp the elastomeric ring 206 along a direction perpendicular to the axis of its body, i.e., from the inlet end to the outlet end. As result, a liquid or air tight seal is created between the elastomeric ring 206 and the nozzle 208.

In some embodiments, in one step, e.g., between the step of FIG. 9A and FIG. 9B, oxygen plasma treatment may be applied to the elastomeric ring 206 or the nozzle 208 such that a surface characteristic thereof is changed. For example, its surface might become hydrophilic. With additional procedures of clamping and heating, a hydrogen bond may be formed between the elastomeric ring 206 and the nozzle 208. As such, friction and seal between the elastomeric ring 206 and the nozzle 208 is increased. The foregoing plasma processing may serve to reduce manufacturing cost and increase assembly efficiency and accuracy. Moreover, the oxygen plasma treatment may be applied before the nozzle is inserted into the elastomeric ring, during the insertion of the nozzle into the elastomeric ring, or after the nozzle is partly inserted into the elastomeric ring entirely.

In certain embodiments, in one step, as shown in FIG. 4, an inclined surface 2068 of the elastomeric ring 206 is present post assembly of the transfusion apparatus 200. In fact, with reference to FIG. 5A, the inclined surface 2068 of the elastomeric ring 206 is continuously present. The inclined surface 2068 corresponds to the inlet end of the nozzle 208 and defines the dimension of the unoccupied volume 2048. Also, the inclined surface 2068 forms a continuously widening cone-shaped wall of the elastomeric ring 206 from its intersection with the nozzle 208 towards the cap 210. As such, the inclined surface 2068 prevents the elastomeric ring 206 from protruding into and obstructing the liquid path due to deformation or manufacture tolerance of the components. Moreover, because the cap 210 is entirely flat facing the receptacle 204, no part of the cap 210 extends into the receptacle 204 to further deform the elastomeric ring 206. As such, the elastomeric ring 206 is only minimally, or even not, deformed by the cap 210. Accordingly, the inclined surface 2068 exists after the following steps: (i) the receptacle 204 is covered by the cap 210; and (ii) the engagement between the casing 212 and the check nut 202. Therefore, furthermore, the inclined surface 2068 continues to exist even after the step of removing the cap 210 from the receptacle 204.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An assembly method of an apparatus suitable for pressurized liquid transfusion, comprising:
preparing an elastomeric ring having a first end and an opposite second end, between which is a through hole having an internal contour, wherein the elastomeric ring further includes an outer contour;
tensioning the elastomeric ring to allow a nozzle to be inserted from the first end into the through hole;
aligning the nozzle with the second end of the elastomeric ring to create a nozzle assembly;
adapting the nozzle assembly into an internal volume of a receptacle, wherein a height of the elastomeric ring is greater than that of an inner wall of the receptacle by a predetermined height;
disposing a cap into a casing, wherein the cap has a flat surface facing the receptacle;
inserting at least part of the receptacle containing the nozzle assembly into the casing, wherein the cap is configured to cover the receptacle; and
engaging the casing with a check nut of an aerosol generating apparatus to secure the nozzle assembly and the cap such that the predetermined height is diminished,
wherein a pressurized liquid medicament is directed to pass through the nozzle assembly to generate aerosol,
wherein the elastomeric ring, the cap and the nozzle define an internal void therebetween, the elastomeric ring being further formed with an inclined surface surrounding an inlet end of the nozzle, and
wherein the elastomeric ring, the cap and the nozzle are further configured to form a proper seal therebetween to prevent any leakage of the pressurized liquid medicament.

2. The method according to claim 1, further comprising:
inserting the nozzle from the first end into the through hole to the extent that the nozzle extends out of the second end of the elastomeric ring and
pushing the nozzle back into the through hole until the nozzle is aligned with the second end so as to create the nozzle assembly.

3. The method according to claim 1, further comprising:
applying force to insert the nozzle into the elastomeric ring such that the elastomeric ring is stretched after the nozzle is inserted.

4. The method according to claim 1, further comprising:
applying force to compress the elastomeric ring of the nozzle assembly such that the nozzle assembly is adapted to fit into the internal volume of the receptacle.

5. The method according to claim 1, further comprising:
adjusting a dimension of the elastomeric ring of the nozzle assembly for being adapted into the internal volume of the receptacle, wherein a diameter of the elastomeric ring of the nozzle assembly inserted into the receptacle is less than that of the elastomeric ring before the reception of the nozzle assembly by the receptacle and less than that of the elastomeric ring after the nozzle assembly is removed from the receptacle.

6. The method according to claim 1, further comprising:
processing the elastomeric ring to change its physical or chemical property.

7. The method according to claim 1, further comprising:
processing the elastomeric ring to increase friction when it makes contact with an other object.

8. The method according to claim 1, further comprising:
processing the elastomeric ring at sections that are in contact with the nozzle.

9. The method according to claim 8, further comprising:
applying a hydrophobic material to sections of the elastomeric ring that are in contact with the nozzle.

10. The method according to claim 1, wherein a surface of the internal contour of the elastomeric ring is uniformly smooth in a micrometer scale.

11. The method according to claim 1, further comprising:
wetting sections of the elastomeric ring to be in contact with the nozzle such that an interface layer containing a wetting material is formed between the elastomeric ring and the nozzle.

12. The method according to claim 11, further comprising:

applying force to the elastomeric ring at a first direction perpendicular to a second direction from the first end to the second end of the elastomeric ring to create a vacuum seal.

13. The method according to claim 1, further comprising:

applying an adherence-enhancing layer between the elastomeric ring and the nozzle such that at least 11 newtons of force is needed to remove the nozzle from the elastomeric ring, wherein the elastomeric ring and the nozzle are free from breakage post removal.

14. The method according to claim 1, further comprising:

adjusting a smoothness of the internal contour of the elastomeric ring such that a static friction between the elastomeric ring and the nozzle is at least 4 newtons.

15. The method according to claim 1, further comprising: treating the elastomeric ring with plasma so as to change a surface characteristic thereof.

16. The method according to claim 1, wherein a surface characteristic of the internal contour is different from a surface characteristic of the outer contour.

17. The method according to claim 1, wherein the inclined surface is formed starting from a border between the nozzle and ends at an intersection between the cap, and the inclined surface is present: (i) after the nozzle assembly is received by the receptacle and covered by the cap; (ii) after the engagement between the casing and the check nut; and (iii) post of removal of the cap from the receptacle, wherein the internal void is further defined by the inclined surface of the elastomeric ring, the cap and the nozzle at the internal volume of the receptacle.

18. The method according to claim 1, wherein the internal void is defined to be substantially U-shaped.

\* \* \* \* \*